United States Patent

Unsworth et al.

Patent Number: 5,846,247
Date of Patent: Dec. 8, 1998

[54] SHAPE MEMORY TUBULAR DEPLOYMENT SYSTEM

[76] Inventors: John D. Unsworth, 365 Lodor Street, Ancaster, Canada, L9G 2Z5; Thomas C. Waram, 207 Charlton Ave. West, Hamilton, Canada, L8P 2E3

[21] Appl. No.: 749,661

[22] Filed: Nov. 15, 1996

[51] Int. Cl.[6] .................... A61F 11/00; A61M 29/00
[52] U.S. Cl. .................... 606/108; 606/200; 606/198
[58] Field of Search ................ 606/1, 106, 108, 606/78, 151, 191–200

[56] References Cited

U.S. PATENT DOCUMENTS

| | | |
|---|---|---|
| 3,868,956 | 3/1975 | Alfidi et al. . |
| 4,503,569 | 3/1985 | Dotter . |
| 4,512,338 | 4/1985 | Balko et al. . |
| 5,334,168 | 8/1994 | Hemmer . |
| 5,370,109 | 12/1994 | Cuny ........................... 606/198 |
| 5,653,736 | 8/1997 | Glastra ......................... 606/198 |

FOREIGN PATENT DOCUMENTS

| | | |
|---|---|---|
| 0 418 381 | 3/1991 | European Pat. Off. . |
| 0 717 961 | 6/1996 | European Pat. Off. . |
| 94/24962 | 10/1994 | WIPO . |

Primary Examiner—Glenn K. Dawson

[57] ABSTRACT

Tubes made from shape memory alloy (SMA) assume their original shape when heated to their austenite finish temperature by directing photo-thermal or electrical energy inside parts of the tube using an optical fiber or conductors, the remainder of the tube acting as a heat sink. Using this method of photo-thermal heating or joule heating, virtually any predetermined shape can be made from tubes, or objects having tubular passages, in a controlled manner with very little heat being transferred to the material surrounding the outside of the tube. The optical fiber may also be used to detect the transformation of the material at the heated site from martensite to austenite and the temperature of the heated site, and use this information to control deployment of the device and reduce overheating of the tube and the material surrounding the outside of the tube.

26 Claims, 8 Drawing Sheets

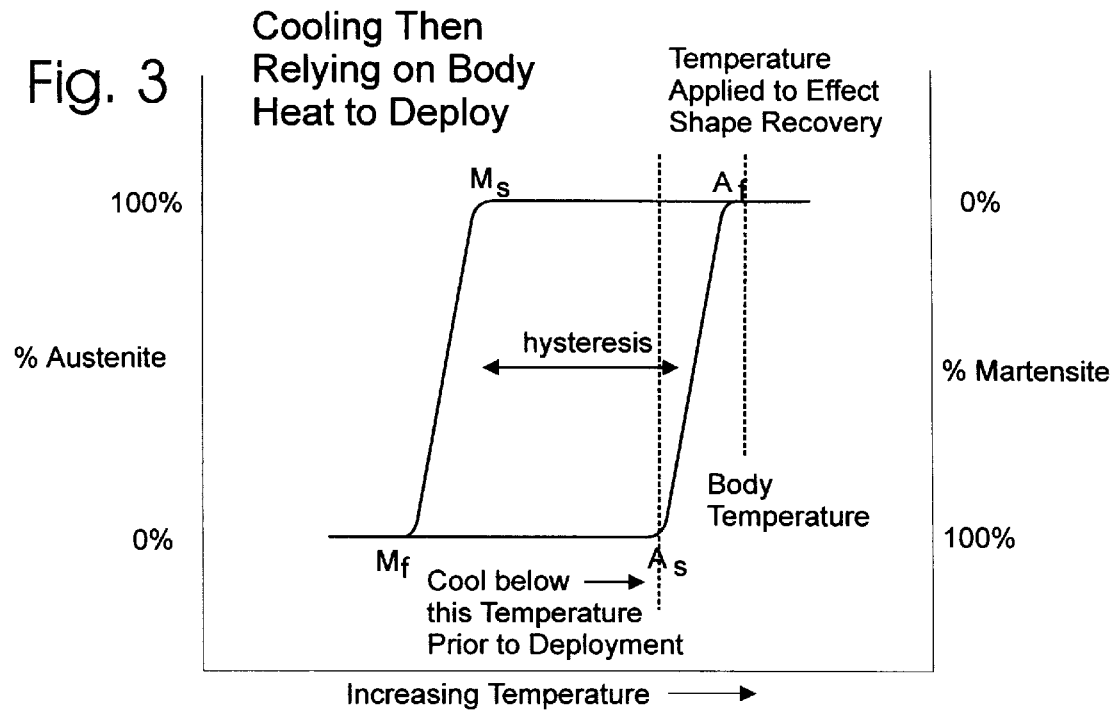
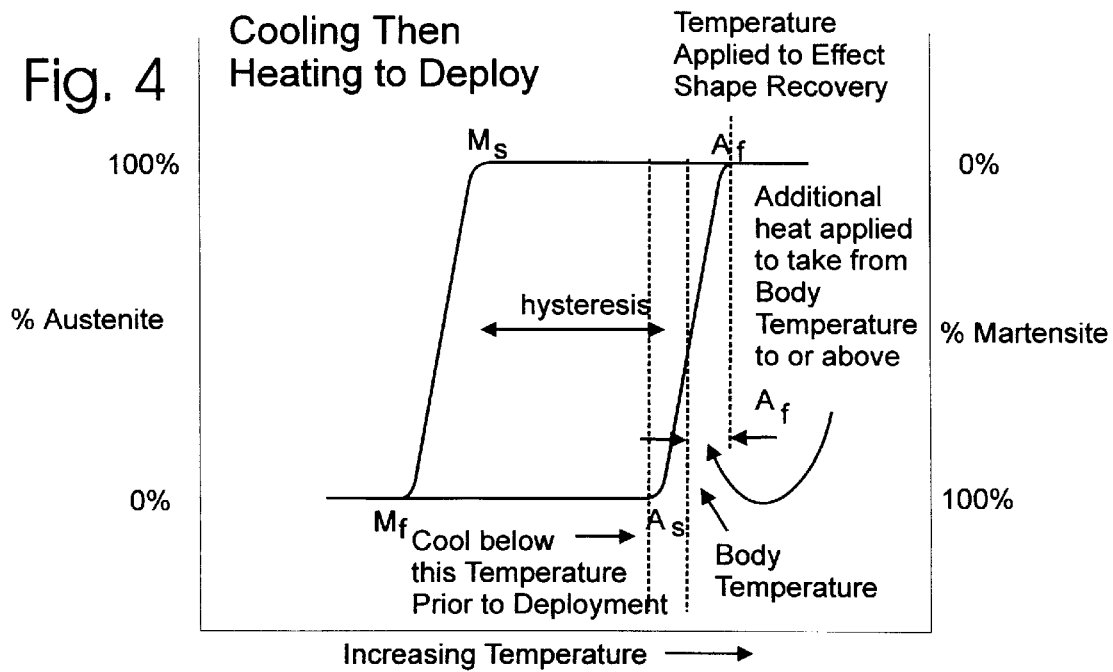

SHAPE MEMORY TUBULAR DEPLOYMENT SYSTEM

FIELD OF THE INVENTION

This invention relates to shape memory materials, including shape memory alloys and improved methods for controlling their shape recovery.

INTRODUCTION TO THE INVENTION

Materials, both organic and metallic, capable of possessing shape memory are well known. An article made of such materials can be deformed from an original, high temperature configuration to a second, low temperature configuration. The article is said to have shape memory for the reason that, upon the application of heat alone, it can be caused to revert, or to attempt to revert, to its high temperature shape, from its low temperature configuration, i.e. it "remembers" is original, high temperature shape. The high temperature shape is imparted, that is, "memorized", during an operation known as shape setting, in which the material is constrained to the desired high temperature shape at elevated temperature, and kept there for a finite amount of time.

Among metallic alloys, the ability to possess shape memory is a result of the fact that the alloy undergoes a reversible solid state phase transformation from an austenitic state to a martensitic state with a change in temperature. This transformation is sometimes referred to as a thermoelastic martensitic transformation. An article made from such a shape memory alloy (SMA), for example a wire, is easily deformed from its original high temperature or austenitic configuration to a new configuration when cooled below the temperature at which the alloy is transformed from the austenitic state to the martensitic state. The temperature at which this transformation begins is usually referred to as the $M_s$ temperature (the martensite start temperature), and upon continued cooling the temperature at which it finishes, the $M_f$ temperature (the martensite finish temperature). The wire changes from a rigid state with a relatively high yield strength, in its austenitic form, to a state in which it is easily deformable, with a relatively low yield strength, in its martensitic form, in which it is able to sustain significant plastic-like deformation, at an almost constant stress level, as the result of the realignment of crystallographic twins which formed during cooling from the austenitic to the martensitic state, in a process known as self-accommodation.

When an article thus deformed is warmed to the temperature at which the alloy starts to revert back to austenite, referred to as the $A_s$ temperature (austenite start temperature), the deformed object will begin to return to its original configuration; with continued heating the object will reach a temperature referred to as the $A_f$ temperature (the austenite finish temperature), the temperature at which the reversion to the high temperature configuration is complete.

Devices made from SMA rely on this property of shape memory to achieve their desired effects. That is to say, they rely on the fact that when an SMA element is cooled to its martensitic state and is subsequently deformed, it will retain this deformed shape due to the fact that in this state it is able to easily sustain deformation. However, when it is heated to its austenitic state, the original high temperature austenitic shape will be recovered and the shape in the austenitic form will be relatively rigid and not easily deformable.

One characteristic of SMA is that there is a large temperature hysteresis as the alloy is transformed between austenitic and martensitic states, so that reversing of the state of an SMA element may require a temperature excursion of several tens of degrees celsius. This characteristic offers both problems and opportunities for designing devices that are implanted in the body. The body temperature, and thus the temperature of the device when it assumes the body temperature after deployment, should in most cases be above $M_s$. Otherwise, the device will be too easily deformed and will lack the structural rigidity and strength necessary to effect its purpose (SMA is rigid and strong from $A_f$ to $M_s$; but becomes much less rigid and will sustain deformation under relatively low stress levels as it goes from $M_s$ to $M_f$). To prevent the device from deploying when it assumes the body temperature, the body temperature should be controlled such that it's below $A_s$. This prevents the device from assuming its memorized high temperature shape, which starts at the $A_s$ temperature and is completed at the $A_f$ temperature. The most straightforward means of deployment is to use SMA material in which the body temperature is between $M_s$ and $A_s$ and the device is heated to or above $A_f$. This method is illustrated graphically in FIG. 2.

However, one constraint that has complicated the development of such devices for use in medical devices, is that human tissue cannot be heated or cooled beyond certain relatively narrow limits (approximately 0° to 60° C. for short periods) without suffering temporary or permanent damage. Because of the large temperature hysteresis between phase transformations, present shape memory materials would need to be heated close to this upper temperature limit of 60° C., in order to reach $A_f$, if the body temperature was between $M_s$ and $A_s$. Due to this temperature limitation, many devices that are implanted in the body are cooled below $A_s$ prior to and while being implanted to prevent premature deployment. Once in place, they then rely on body heat to heat them from $A_s$ to $A_f$ to transform them into their austenitic memorized shape. The $A_f$ temperature for such devices is at or below body temperature thereby ensuring full deployment. This method is illustrated graphically in FIG. 3.

Another approach is to use a device made in such a way that body temperature is between $A_s$ and $A_f$, in which case cold saline is used to cool the device prior to and while being implanted to prevent premature deployment, and then when the device is properly located, hot saline is pumped around the device to heat the device above $A_f$ and thereby transform it into its memorized austenitic shape. This method is illustrated graphically in FIG. 4.

The present invention makes it feasible to have body temperature between $M_s$ and $A_s$ since the device can be heated to higher temperatures, to achieve transformation to the memorized shape at $A_f$, without harming human tissue. This obviates the need to cool the device prior to and while it is being implanted.

The prior art references most relevant to the present invention are the products described by Dotter ("Transluminal Expandable Nitinol Coil Stent Grafting: Preliminary Report," Radiology, 147, April, 1983, pp. 259–260 and U.S. Pat. No. 4,503,569), Cragg, et. al., ("Nonsurgical Placement of Arterial Endoprosthesis: A New Technique Using Nitinol Wire," Radiology, 147, April, 1983, pp. 261–263), Alfidi, et. al., U.S. Pat. No. 3,868,956 and Balko (Transfemoral Placement of Intraluminal Polyurethane Prosthesis for Abdominal Aortic Aneurysm, Journal of Surgical Research, 40, April, 1986, pp. 305–309; and U.S. Pat. No. 4,512,338). The Dotter article discloses the use of a nitinol SMA material having a $A_f$ temperature or transition temperature of 130° F. to 140° F. (54.4° C. to 60° C.), thus, requiring an injection of hot saline to cause the material to recover its high temperature coil shape. Despite the specific requirement for hot saline, the Dotter patent claims a nitinol material with a transition temperature in a range at or above normal body temperature, which is approximately 37° C. Because the Dotter patent does not incorporate any means to restrain the coil during insertion, the placement procedure requires an initial injection of cold saline to insure the material does not undergo shape recovery during insertion, followed by a second injection of hot saline to encourage shape recovery. Cragg utilizes a threaded adapter on one end of the coil to hold it during placement. Alfidi discloses an appliance expansible by the application of electrical heating and Dotter disclosed using a brief pulse of electricity through a device to provide the transformation temperature. The use of electricity to heat the entire device was also disclosed in U.S. Pat. No. 5,334,168 issued to Chad G. Hemmer on Aug. 2, 1994. Balko discloses a nitinol shape memory wire with a transition temperature below body temperature. In order to prevent the stent from changing shape while being positioned in the body it is enclosed in an insulating sheath.

All of the stents described in the prior art patents and articles suffer from the same deficiencies. The stents and delivery systems are not designed to work together to allow accurate and controlled placement of the device, while the shape-memory property of the nitinol materials is utilized; maximum advantage of this property cannot be realized because the design of the prior art delivery systems does not adequately control the transformation of the stent from its cold temperature form to the pre-set form attained above its $A_f$. A potential problem of nitinol alloys with a high $A_f$ (i.e., 130° F. to 140° F.; or 54.4° C. to 60° C.) is that if they are heated in the conventional way, that is: heating the entire device all at once either with hot saline or by passing an electrical current through it, too much heat might be transferred to the surrounding tissue, causing tissue damage. Unrestrained nitinol stents having an $A_f$ below body temperature require rapid placement as they will start transforming to their original shapes as soon as they are introduced into the body or blood stream. A method of restraining a stent to prevent it from prematurely deploying is disclosed by U.S. Pat. No. 5,147,370 issued to Thomas O. McNamara and Gregory Mednik on Sep. 15, 1992, but this stent relies on the heat of the body to generate the transformation temperature and thus the deployment of the stent cannot be interrupted or controlled, once the restraints are released.

Thus, there is a need for a stent and delivery system that overcomes these problems.

For many purposes, it would be desirable to have a method of heating the device that is unobtrusive and efficiently transfers the energy to the device so that little excess heat energy is transferred to the area surrounding the device during deployment. This is important as one would like to have a relatively high transformation temperature for two reasons. First, the device could have an $A_s$ above body temperature and thus could not deploy prematurely due to heating caused by body temperature. Second, the device could have a $M_s$ below body temperature thus ensuring that the device would remain rigid in its austenitic phase after deployment when it returns to ambient body temperature. Such SMA materials are readily available, for example a nickel titanium alloy with a composition of 44.435 weight % titanium and 54.430 weight % nickel, as described by Manach and Favier (P. Manach and D. Favier, "Comparison of Homogeneous Shear and Tensile Tests on a Ni—Ti, Shape Memory Alloy", *Proceedings of The International Conference on Martensitic Transformations,* 1992, pp 941–946).

It would also be desirable to be able to change the shape of the device gradually in a controlled manner so that the device could be relocated prior to final deployment. It would also be desirable to be able to bend the end of the device in a number of different directions prior to compete deployment allowing it to be guided around obstructions. It would also be desirable to have a device that could be implanted and later modified while still in place. Finally it would be desirable to be able to detect when the section of the tube at the point of heating has changed into its austenitic phase and also detect the temperature of the tube at the place of heating and adjacent areas, so that unnecessary heating could be avoided.

All previous methods of heating various cross-sections of SMA materials have involved the heating of all of the material contained in the device in a simultaneous and global fashion, that is, a one time, bulk heating event. The difficulty with this approach is that it does not take advantage of the many shapes that are possible prior to full deployment of the device. The partial deployment of a device might be advantageous, as it would allow one to preferentially bend it in a direction that might avoid an obstruction. This might assist in properly locating it, prior to full deployment. Selectively transforming the shape of the device, at different locations on the device, also allows for modifications in the shape and thus a standard device can be used to create many different shapes for different anatomical circumstances. Also a final shape may be generated by transforming only parts of the device, and then one might be able to have the device return to approximately its original shape by transforming other parts of the device. This would allow for the deployment and subsequent removal of the device if the operation was aborted.

For devices that do not rely on body temperature to heat the device above $A_f$, heating the entire device above $A_f$ may result in excessive heat transfer to the surrounding tissue. If only one part of the device is heated at a time, the heat input can be turned off, allowing any excess or residual heat to dissipate, the device itself acting as a heat-sink. Another disadvantage of deploying all of the material in the device at one time is that it can cause a considerable whipping motion, especially if the device forms into a helical coil. If placed inside a blood vessel, this can result in endothelial damage with a highly thrombogenic surface. The proposed device would deploy in an incremental, controlled fashion and therefore there would not be any whipping motion.

SUMMARY OF THE INVENTION

The invention is a method of shaping tubes made of SMA and objects made of SMA that contain tubular passages. An efficient and unobtrusive means of delivering photo-thermal energy to such devices made of SMA would be an optical fiber with a photo-thermal energy source. The invention includes a number of methods that concentrate the photo-thermal energy delivered by a photo-thermal source, for example a laser, to a relatively small area of the SMA material. This permits a progressive and controlled means of deploying the devices that incorporate SMA material. It also permits rapid heat dissipation with little heat transferred to the material surrounding the device. Of course the device described might also be cooled prior to deployment or during or after its deployment, using the usual methods of introducing cold saline around the stent; however the present invention has features that should obviate cooling.

In one of the preferred embodiments of the invention, the terminal end of the optical fiber could include a collimating lens that would direct the energy down the tubular passage to which it is detachably attached. This embodiment is especially well suited to devices that include tubes that have a relatively small radius.

This method includes means by which the energy that is directed down the tube by the optical fiber is absorbed by different parts of the walls of the tube in a predetermined manner. In most cases, this causes the tube to bend in the desired configuration from the distal end (the end most remote from the connection to the optical fiber energy source) to the proximal end (the end that is detachably attached to the optical fiber energy source). The principal means by which this occurs is due to the fact that the amount of heating that occurs on a given part of the interior of the tube will depend partly on the angle at which the photo-thermal rays strike the surface. Typically the smaller the angle between the incident ray and the normal from the surface at the point of incidence, the greater the amount of total heat energy that will be transferred to that surface. The amount of heat transferred is also related to the absorptivity and reflectivity of the material at the point of incidence. Also the absorptivity depends on the frequency of the incident photo-thermal energy and therefore, the said frequency can also be used to control the total photo-thermal energy transferred to the incident surface.

For example: consider a tube that has a helical spring shape when the SMA material is in the austenitic phase ($A_f$ to $M_s$ after heating to or above $A_f$); and it is then cooled to its martensitic phase below $M_s$, and then it is deformed into an approximately straight tube with a right angle bend at its terminal end. For example, if the interior of the tube is mostly free of oxide and therefore relatively shiny, most of the photo-thermal energy passing down the tube will be mostly reflected off the interior wall surfaces, except where the tube is bent. Where it is bent more photo-thermal energy will be absorbed and local heating will occur. The local heating will cause that area to return to its austenitic phase and the said area will thereby return to its memorized shape, in the example: part of a spring. This bending will cause the area directly adjacent to the initial point of heating to absorb more of the photo-thermal energy compared to the unchanged and relatively straight reflective tube length. As more energy is directed down the tube, the configuration of the helical spring will form gradually from the distal end to the proximal end as this process of local absorption, bending and further absorption and bending, goes forward to the proximal end. The tube can be extruded out of a catheter with a compliant end, as it is being deployed, thereby reducing the heat transfer from the tube to the surrounding tissue. The catheter end can be made from elastic material allowing the device to form its high temperature shape within the end of the catheter tube without binding.

Instead of a vacant lumen, an optical fiber can occupy all or a part of the interior of the tube and act as a light guide. In this preferred embodiment, the optical fiber occupying the lumen of the SMA tube can be chosen to leak the thermal energy that is directed down the fiber, approximately normal to the longitudinal axis when the optical fiber is bent in an arc equal to or less than a particular radius, the "Transfer Radius". The Transfer Radius will depend upon the type of optical fiber used and is an inherent characteristic of optical fibers. The interior of the tube could be coated or treated so as to absorb as much thermal energy as desired. By choosing a suitable optical fiber for this purpose one can cause the photo-thermal energy to be transferred to the interior walls of the tube, immediately adjoining the part of the optical fiber and tube at the point at which the optical fiber is bent to the Transfer Radius. This preferred embodiment operates in an identical way to the previous preferred embodiment, except that this preferred embodiment depends upon the leakage of the photo-thermal energy though the outer surface of the optical-fiber as above described. This preferred embodiment permits more control of the amount of photo-thermal energy that is absorbed by the inner surface of the tube at a point of bending as the composition of the optical fiber is more stable and uniform that that of the SMA tube.

As can be seen this method of deploying a SMA device allows for much greater control over the shape recovery process than simple bulk heating. One can stop deploying the device at any point in its return to its original austenitic shape. One can vary the rate of deployment by varying the amount of energy delivered to the tube. Since the phase change from martensite to austenite on heating is endothermic, when the phase change occurs, a significant part of the total photo-thermal energy that is applied to the interior of the tube will be used in the process of the phase transformation from martensite to austenite and a minimal amount will be transferred to the material surrounding the outside surface of the tube.

Since the heat is applied to the inside surface of the tube, the temperature rise that will occur at the outside surface of the tube, after all of the material in the tube is fully transferred to austenite, will be significantly less than if the tube had been heated from the outside only (eg. by saline heating) or if the bulk material had been heated by resistive joule heating (eg. by passing an electrical current through the whole tube).

Also, when the inside of the tube transforms from martensite to austenite it becomes more reflective, making it less absorptive and less likely to transmit excess heat to the outside walls of the tube. Finally, the segment of the tube along the tube length that absorbs the energy at any one time is small in relation to the full length of the tube, so the rest of the tube acts as a heat-sink dissipating excess heat. The tubular structure of the device also reduces its material mass and therefore reduces its thermal mass, making excessive heat transfer to the surrounding tissue less likely. The other advantage of the present invention is that the device itself and the means by which the photo-thermal energy is delivered to the device can be very small in the direction normal to its longitudinal axis prior to deployment, making it suitable for inserting in blood vessels. Virtually any shape can be memorized into the tube in its austenitic phase, by the shape setting process, and then it can be deformed below the $M_f$ temperature into an approximately straight tube for insertion.

The three dimensional recovery path that the SMA tube follows is dependent on the deformation path that was used to change the tube from its austenitic memorized shape to an approximately straight tube configuration below $M_f$. Therefore, it is possible to control the directional mode of recovery of the device. Depending upon the method of deforming the device, below $M_f$, into its martensitic form as an approximately straight tube, the device can be deployed in different orientations with respect to the longitudinal axis of the straight and as yet unbent tube. For example, in the case of the tube formed into a helical spring, given as an example above: if the spring is deformed in the martensitic state, below $M_f$, by unwinding it normal to its longitudinal axis, the spring will undergo shape recovery on heating to its transformed austenitic phase, normal to the longitudinal axis of the straight tube; if it is deformed by pulling the spring parallel to its longitudinal axis, the spring will undergo shape recovery parallel to the longitudinal axis of the straight tube.

The means by which the directed energy is directed to different parts of the interior surface walls of the tube can be effected by a number of means: the relative reflectivity and absorption of photo-thermal energy of the surface of the tube walls is the simplest case.

In another preferred embodiment of the invention the transfer of photo-thermal energy to different parts of the interior surfaces of the tube can also be effected by pushing the optical fiber down the said approximately straight tube, withdrawing a fiber from the said tube, or pushing the said tube forward and off the end of the optical fiber. In this case the terminal end of the optical fiber is formed into a shape that causes the photo-thermal energy to be redirected normal to the longitudinal axis of the optical fiber. This is known as a side-firing optical fiber. The end of the optical fiber can have various attachments that will effect this purpose or alternatively the fiber itself can be fabricated so that it side-fires at its end. For example: the end of the optical fiber can be made side-firing by beveling the end at an angle of approximately 45° and then applying a mirrored surface to the said beveled end. This will result in the photo-thermal energy, that is projected down the optical fiber, being projected as a spot on the inside of the tube, into which the fiber is passed. Another example of a side-firing end of the optical fiber can be made by honing out a concave cone-shaped recess in the end of the optical fiber, and then applying a mirrored surface to the said concave cone. In this case, the photo-thermal energy that is projected down the optical fiber will project onto a ring shaped or cylinder shaped section of the inside surface of the tube in which the optical fiber is contained. In addition to the two examples given above, many other optical attachments and means of modifying the end of the optical fiber are commercially available.

These preferred embodiments permit the gradual deployment of the tube in a controlled manner. It is possible to heat only a small ring, cylindrical section, or spot on the inside of the tube, and this allows the rest of the tube to dissipate the thermal energy and thereby reduce the possibility of heat damage to the surrounding tissue. Again the heat is applied to the inside surface of the tube and therefore the heat transfer to the outside of the tube, and from the outside of the tube to the surrounding tissue is minimized. If the tube is inside a delivery catheter, and the optical fiber is inside the tube, the tube can be slowly extruded out of the catheter at approximately the same rate as the tube is transformed to its austenitic state by the heat energy of the side firing optical fiber end. The end of the delivery catheter can be sufficiently compliant so as to allow the heating and transformation to occur inside but near the distal end of the catheter. This has the advantage of insulating the surrounding tissue from the ring shaped section, cylinder shaped section, or localized spot where the heat is being applied, but does not allow the tube to jam inside the delivery catheter. If the tube is heated by a side-firing optical fiber that is designed to project a spot of photo-thermal energy on the inside of the tube, rather than a ring, the optical fiber must be rotated to permit the entire circumference of that part of the tube to be exposed and heated, if so desired. There are however cases in which the optical fiber would not be fully rotated such that the entire arc length of the inside circumference is exposed to the impinging photo-thermal energy. One such case would be where it is desirable to bend the tube to avoid an obstruction. For example: if a cylindrical section of the tube was stretched longitudinally below the $M_f$ temperature and one heated only one spot or patch of the inside of the said tube to above the $A_f$ temperature, this would cause the tube to shrink at the point of heating and the tube would bend; heating a certain spot or patch of the said tube opposite the first spot or patch would cause the tube to reduce the curvature imparted by the first patch and the tube would somewhat straighten. Another way of bending the tube would be to heat a small cylindrical section on a part of the tube that has a bend memorized into that part of the tube. In this case if the tube needed to be approximately straightened again, heat could be applied to another cylindrical section, in proximity to the first bend, that also has a bend memorized into it that is opposite in direction to the first said bend.

Because this system permits the heating of small, localized areas, the tube can be bent in many different directions, limited only by the shapes that are memorized by the tube. If the radius of the curves in the tube are not too great at the spots where the tube has been heated and thereby transformed, the optical fiber can also be pushed back down the tube to later heat another spot and thereby bend the tube again prior to full deployment.

The location of the laser in the tube at any time can be monitored by simply etching or printing marks on the inside of the tube, and then using a optical splitter adjacent to the heat source to view the surface of the inside of the tube. As well as permitting one to visually view the inside surface of the tube during heating, one can also visually monitor the transformation of the metal from its martensitic state to its austenitic state due to the different reflectivity and appearance of the surface of the metal in the two states. The martensitic phase scatters light more than the austenitic phase[1]. Photo-thermal sensors may also be employed at the said splitter to detect the temperature of the metal at the spot of heating and at adjacent areas. Temperatures of the tube could also be indirectly monitored by viewing biocompatible thermochromatic dyes, liquid crystals or similar materials on the inside of the tube that would change color or state at different temperatures. The feedback of this information would allow the operator to manually or automatically vary the location of the tube relative to the distal end of the laser with exquisite accuracy and also the amount of energy delivered down the tube.

In another preferred embodiment of the invention, instead of the transfer of photo-thermal energy to different parts of the interior surfaces of the tube, electrical energy can be applied in a like manner. This is possible because SMA in the austenitic phase has greater electrical resistance than it does in the martensitic phase; it also has sufficient resistance in its martensitic phase to permit joule (resistance) heating if an electrical current is passed through the martensitic material. This permits the use of a probe, in place of the optical fiber, that has instead of a side-firing end, has two electrically conductive rings that come in contact with the inside of the SMA tube. The rings are placed on the outside distal end of the probe, their major planes normal to the longitudinal axis of the probe, and are separated by a gap of insulating material. The rings are connected to insulated wires that pass down the probe to a power supply, which thereby supplies an electric potential between the two rings. This electrical potential can be either direct current (DC), alternating current (AC), or modulated to control the rate of recovery. This preferred embodiment heats a cylindrical section of the inside of the SMA tube, similar to the cylindrical section that is heated by the side-firing optical fiber that has a concave, mirrored end. This preferred embodiment performs and is operated in a similar way to the optical fiber with a side-firing distal end. Instead of having complete contact rings at the distal end of the probe, a section of the rings, located adjacent to each other, but separated in like manner to the complete rings, would allow for a patch or spot to be heated by passing a current between them in like manner to that used for the complete contact rings. This preferred embodiment performs and is operated in the same way to the optical fiber with a beveled side-firing distal end. Because the electrical resistance of SMA material goes up when it changes from its martensitic phase to its austenitic phase, the current flow can be monitored and used as a means of controlling the probe and the current supplied to the probe.

The extruding tube that is detachably attached to the SMA tube can be attached by enlarging the circumference of a cylindrical section at the proximal end of the SMA tube below the $M_f$ temperature so that the outer surface of the cylindrical section forms a strong mechanical friction bond with the inner diameter of the extruding tube of slightly larger diameter, into which it is forced. When the SMA tube is fully deployed one can detach the device from the extruding tube by simply heating the inside of the joint above the $A_f$ temperature which causes the end of the SMA tube to revert to its smaller diameter and thereby separate the device from the extruding tube. Of course the SMA tube could also be larger than the extruding tube and the end could be compressed below the $M_f$ temperature rather than expanded to give a similar result This method would be used to attach a device directly to an optical fiber. Other means of attaching the extruding tube to the device, or the optical fiber directly to the device can be effected by using various mechanical means, such as threaded connections and latches well known to the mechanical art.

DRAWINGS

These and other features, aspects and advantage of the present invention will become better understood with reference to the following description, appended claims and accompanying drawings where:

FIG. 3 is a plot of the transformation temperature thermal hysteresis illustrating changes of a SMA device relative to body temperature, where a device is deployed using only body temperature to heat the device, and uses cooling to maintain the temperature of the device prior to deployment to ensure that the body temperature does not deploy the device prematurely.

FIG. 4 is a plot of the transformation temperature thermal hysteresis illustrating the phase changes of a SMA device relative to body temperature, where the device relies on body heat and on a separate means of heating to deploy the device, and also uses cooling prior to deployment to ensure that the body temperature does not partly deploy the device prematurely.

Figure 8:
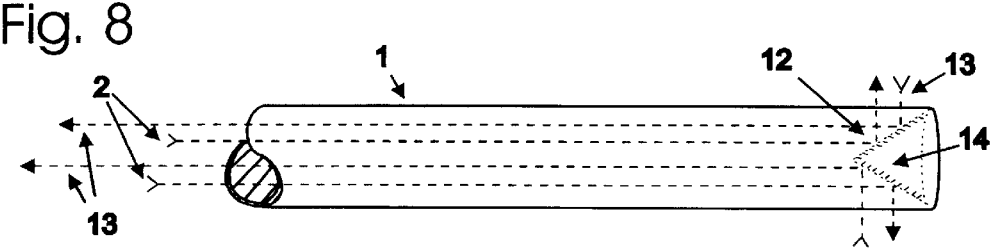
FIG. 8 is a perspective view of the distal end of an optical fiber that is designed to be side-firing, with a concave cone-shaped recess at its distal end that has a mirrored surface that redirects the photo-thermal radiation passing down the tube, in all directions normal to the longitudinal axis of the optical fiber.
Figure 9:
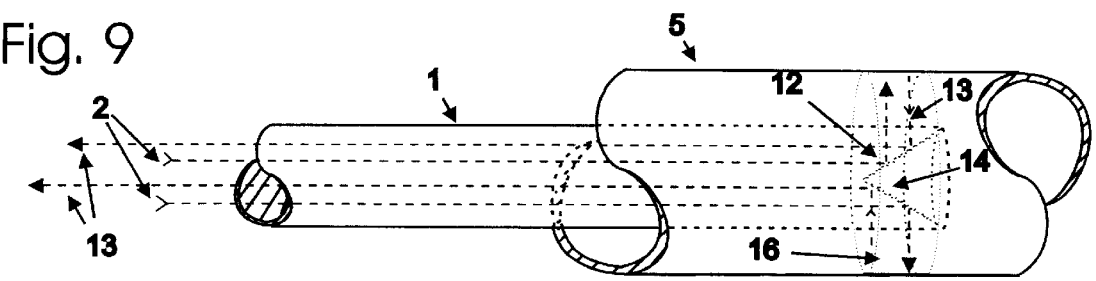

FIG. 9 is a perspective view of the same distal end of the optical fiber illustrated in FIG. 8, but in addition has a section of SMA tube that illustrates the projection of the photo-thermal energy onto a cylindrical section of the tube, and the reflection and radiation of some of the energy off the said entire inner surface of the said SMA tube section and showing it being directed back down the optical fiber.

Figure 10:
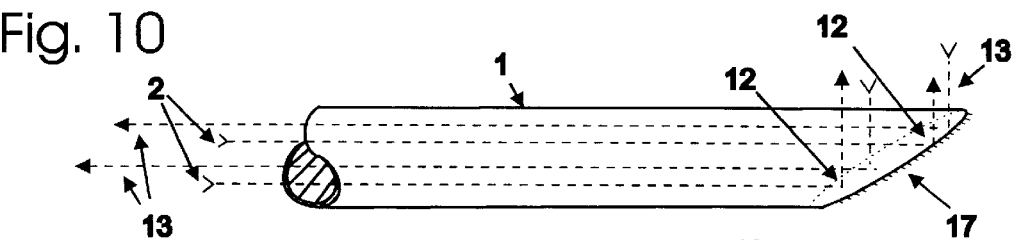

FIG. 10 is a perspective view of the distal end of an optical fiber that is designed to be side-firing, with a mitered end that has a mirrored surface that redirects the photo-thermal energy passing down the tube, in a beam normal to the longitudinal axis of the optical fiber.

Figure 11:
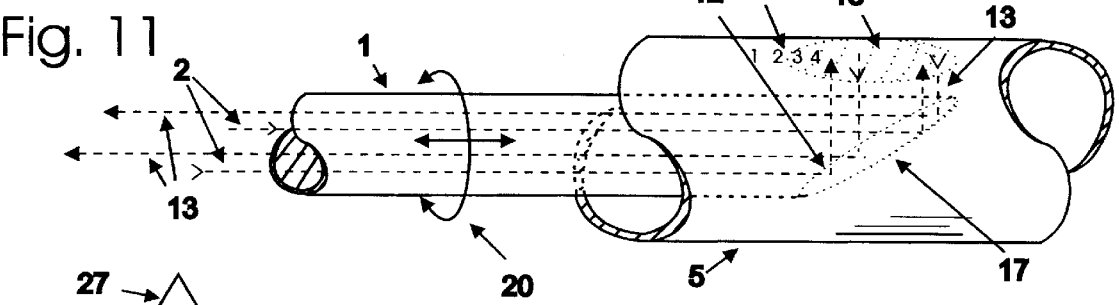

FIG. 11 is a perspective view of the same distal end of the optical fiber illustrated in FIG. 10, but in addition has a section of a cylindrical SMA tube that illustrates the projection of the photo-thermal energy beam on to a patch of the inner surface of the said tube, and the reflection and radiation of some of the energy off the said patch of the inner surface of the said cylindrical tube and showing it being directed back down the optical fiber. FIG. 11 also illustrates that the tube can be rotated about its longitudinal axis and thereby change the location of the said projected patch of photo-thermal energy on different parts of the inner surface of the said cylindrical tube.

Figure 12:
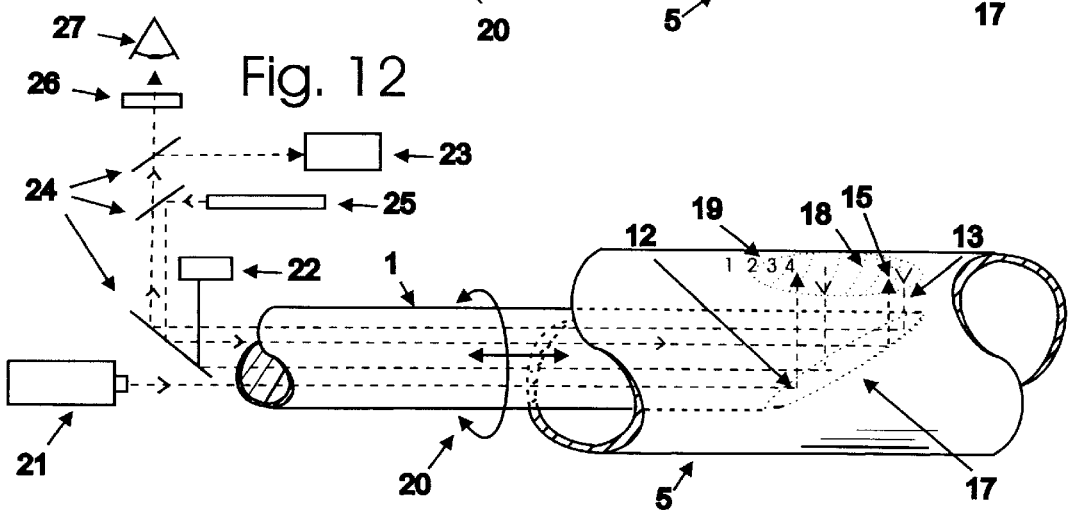

FIG. 12 is a side perspective view of the distal end of the optical fiber illustrated in FIG. 11, but with the addition of the photo-thermal heat source, optical illuminating means, optical detection and radiation detecting means and means for optically viewing the location of the area where the beam of photo-thermal energy is being projected on the inner surface of the cylindrical tube.

Figure 13:
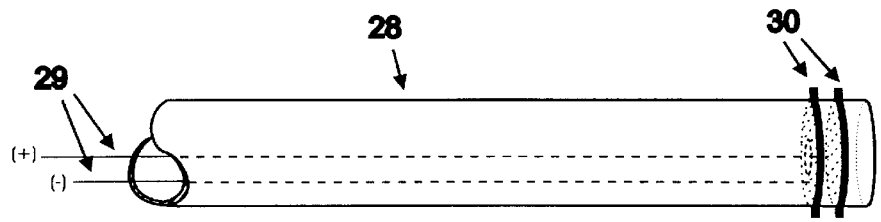

FIG. 13 is a perspective view of the distal end of a probe with two electrical contact rings to which each has attached an insulated wire; the two wires passing down the probe to a power supply that is not shown.

Figure 14:
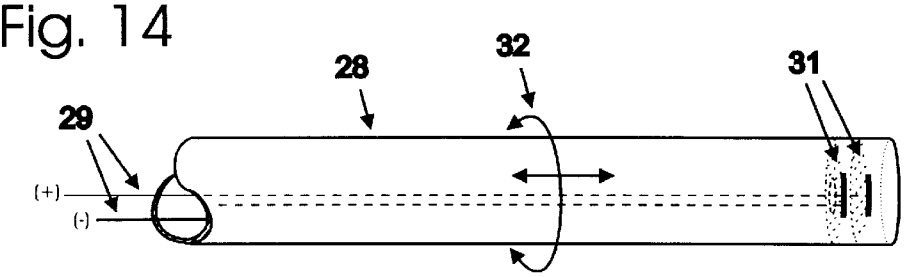

FIG. 14 is a perspective view of the distal end of a probe with two electrical contacts to which each has attached an insulated wire, the two wires passing down the probe to a power supply, not shown. FIG. 14 also illustrates the fact that the tube can be rotated about its longitudinal axis and thereby change the area of contact with the inner surface of a SMA tube into which it might be inserted.

Figure 15:
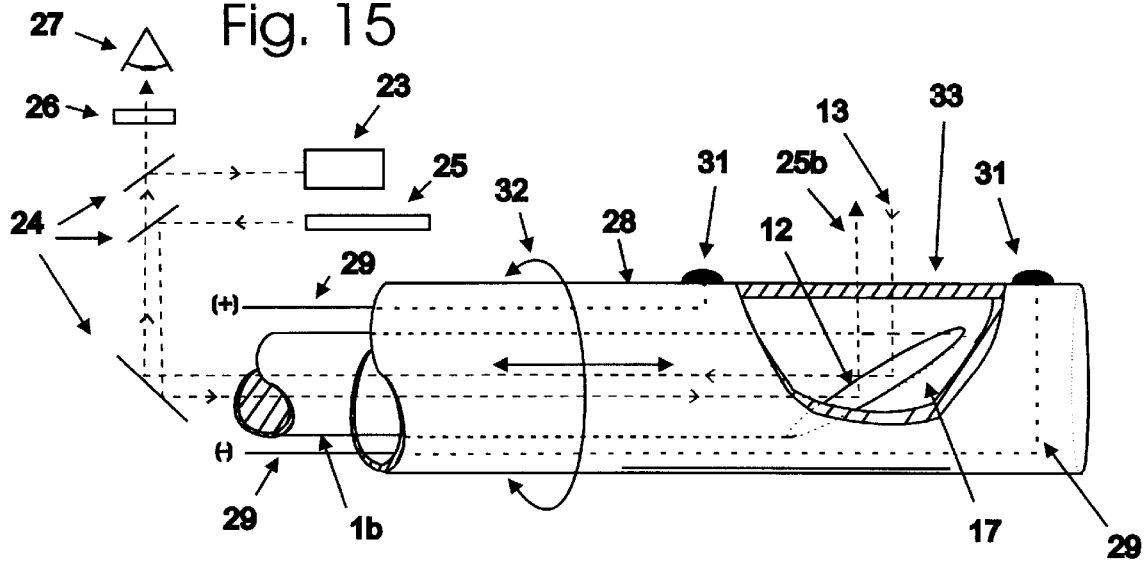

FIG. 15 is a side perspective view of the distal end of the optical fiber similar to that illustrated in FIG. 14, but with the addition of: optical illuminating means, optical detection and radiation detecting means and means for optically viewing the location of the area where the electrical energy is delivered to the inner surface of the cylindrical tube.

Figure 16:
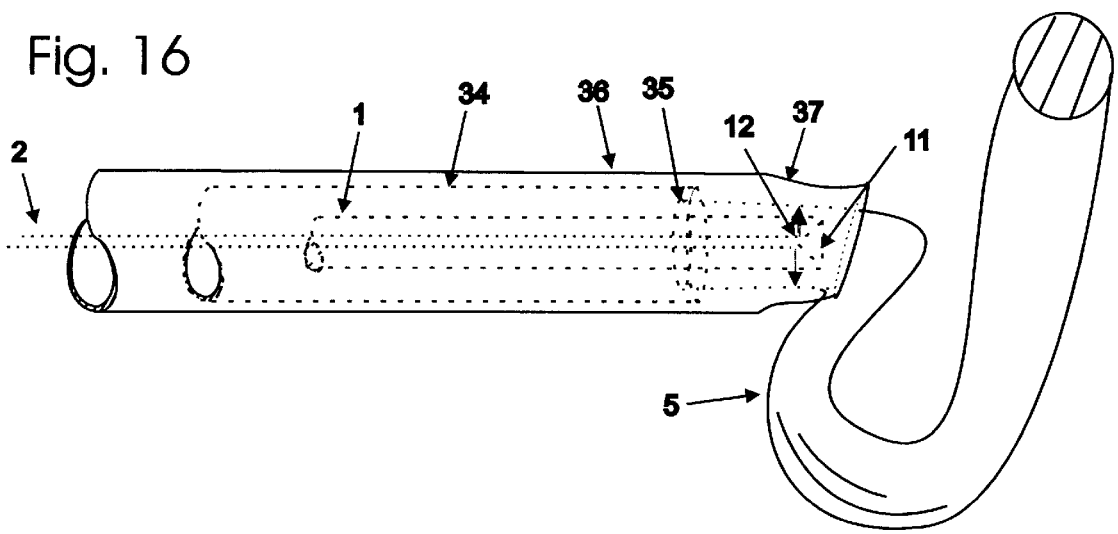

FIG. 16 is a perspective view of the distal end of the cover catheter, extrusion catheter, side-firing optical fiber and SMA tube in the process of recovering into its memorized high temperature shape by the application of photo-thermal energy. FIG. 16 also shows the compliant end of the cover catheter that covers the area of heating, separating it from its surroundings.

Figure 17:
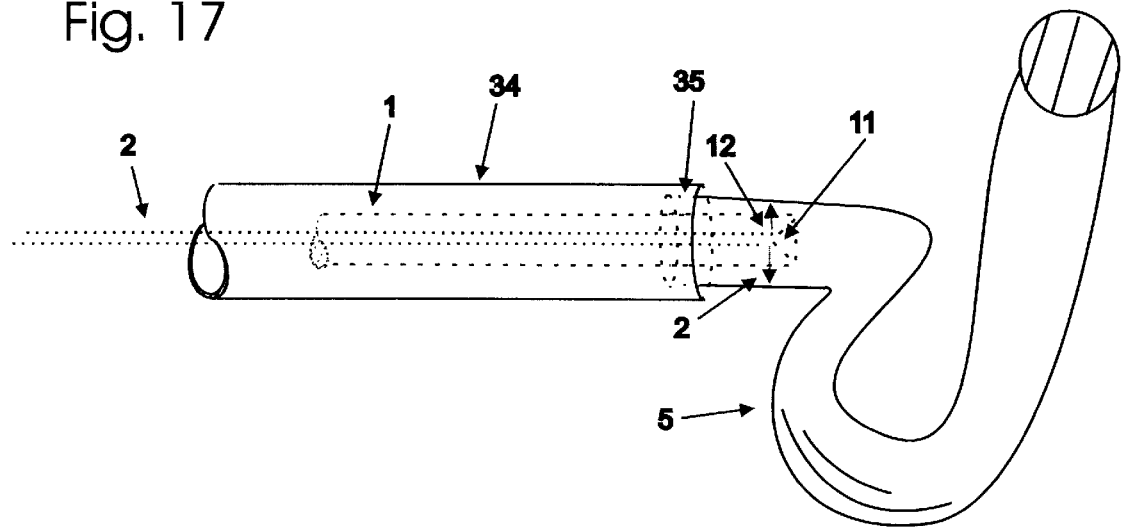

FIG. 17 is the same illustration as FIG. 16 except that the cover catheter is not shown.

Figure 18A:
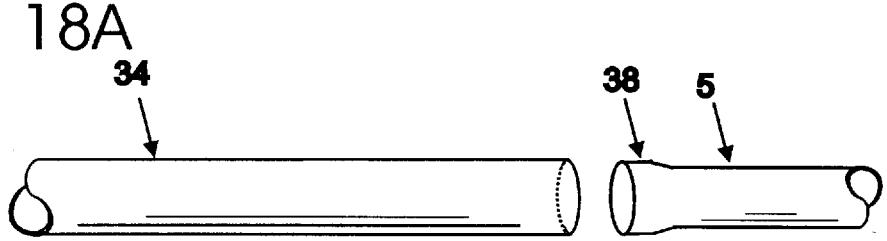
Figure 18B:
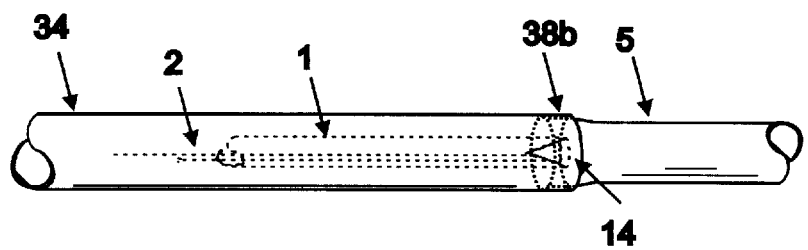
Figure 18C:
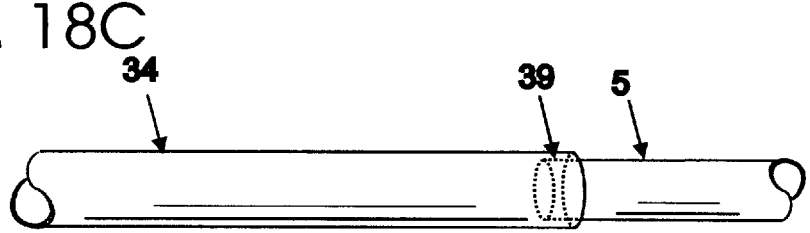

FIGS. 18A, 18B, 18C and 18D are perspective views of the detachable attachment between the extrusion catheter and the SMA tube. FIG. 18A shows the enlarged circumference of a section of the proximal end of the cylindrical SMA tube. FIG. 18B shows the enlarged circumference of a section of the proximal end of the cylindrical SMA tube forming a mechanical friction connection with the inner surface of the distal end of the extrusion catheter. FIG. 18C shows the same proximal end of the cylindrical SMA tube having recovered into its high temperature memorized shape, having approximately the same circumference as the rest of the SMA tube and separated from the inner surface of the extrusion catheter. 14D shows the complete lateral separation between the extrusion catheter and the SMA tube.

DESCRIPTION

A preferred embodiment of the invention is shown in FIGS. 5A, 5B, 5C, and 5D, and comprises as its main elements an SMA tube 5 to which is detachably attached to an optical fiber 1 that can have a collimating lens 3 on its distal end. The photo-thermal energy 2 that passes down the said optical fiber from a remotely connected photo-thermal source is directed down the lumen of the said SMA tube 5 by the said collimating lens 3. The inside surface of the tube then reflects 4 and absorbs 8 the photo-thermal energy that passes down the lumen of the tube 5 depending upon the angle at which the photo-thermal energy passing down the tube strikes the said surface. The distal end of the SMA tube can be bent 6 or closed so that the initial photo-thermal energy that passes down the tube is absorbed at the place of bending 8 or place of closure. If the SMA tube is relatively straight at a temperature below the $A_s$ temperature it will curl-up from its distal end to its detachably attached proximal end as the photo-thermal energy is absorbed and the SMA material is heated above its $A_f$ temperature, first at the distal end of the tube, and then progressively back to the detachably attached proximal end as the bending of the tube and consequent increase in absorbency of photo-thermal energy advances in the same direction, all as described above. The collimating lens 3 assists in directing the photo-thermal beam down the tube, but may not be required depending on the dimensions of the SMA tube. The inner surface of the tube can be acid etched to make its surface shiny and thus reflect the photo-thermal energy that is directed down the tube until it is bent sufficiently so that the photo-thermal energy 2 is absorbed rather than reflected. Rather than being etched the inner surface of the tube can be coated or treated to provide a surface with the desired reflectance and absorbency by many conventional means. The interior surface can also be patterned to assist in increasing or decreasing the relative reflectance and absorbency at different parts of the tube. The detachably attached connection 7 between the optical fiber and the tube can be accomplished by a number of means, including a simple friction coupling that would allow detachment once the fully deployed device was anchored and provided sufficient resistance to allow the separation of the friction connection by simply pulling and twisting the optical fiber. The two could also be connected by a threaded connection or latch or by means illustrated in FIG. 18 and described below.

Figure 1:
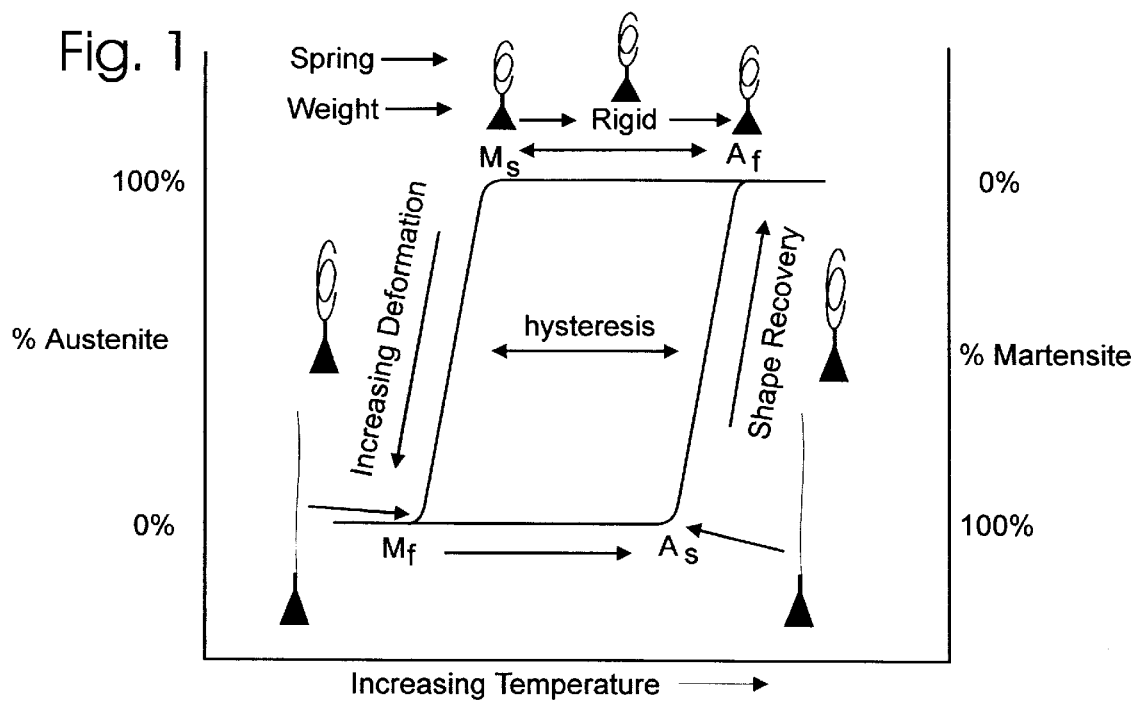
FIG. 1 is a plot of the transformation temperature thermal hysteresis that illustrates the effect of temperature on the relative percentages of austenite to martensite in SMA material and the effect of changing temperatures on the rigidity and shape of the device (Adapted form: See *Using Shaped Memory Alloys Actuator Design,* by Thomas Waram, 2nd Ed., ISBN: 0-9699428-0-X.)
Figure 2:
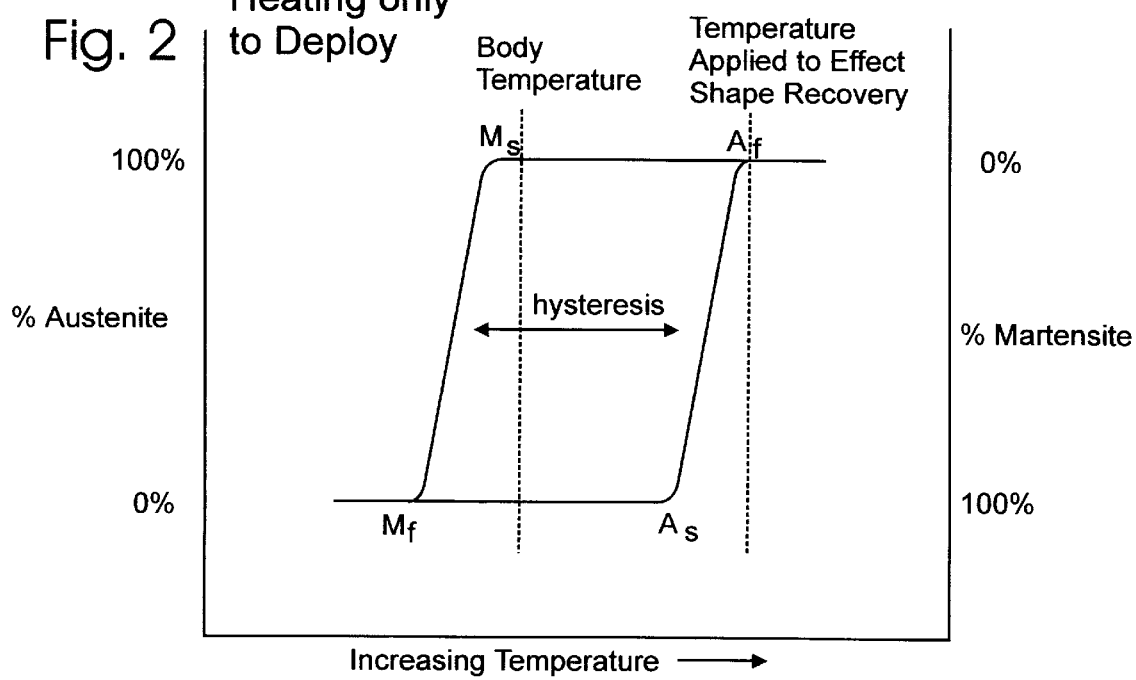
FIG. 2 is a plot of the transformation temperature thermal hysteresis of a SMA device relative to body temperature, where a device is deployed using a heat source other than the heat of the body.
Figure 5A:
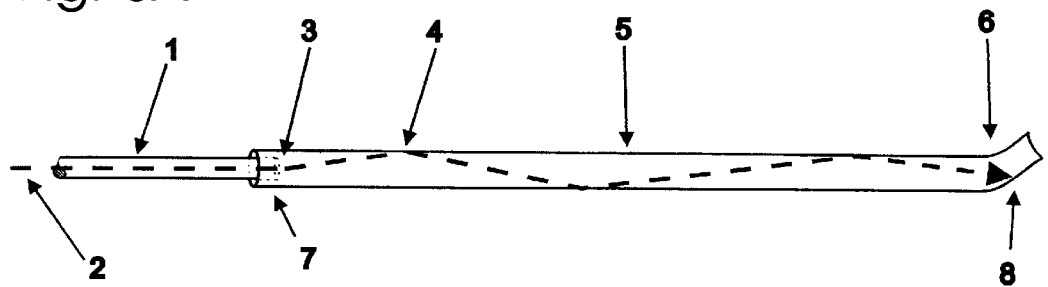
FIGS. 5A, 5B, 5C and 5D are perspective views of a SMA tube detachably attached to an optical fiber; and illustrating a progression of four views of the SMA tube undergoing recovery into its high temperature memorized shape sequentially from FIGS. 5A to 5D upon application of photo-thermal heating delivered by the optical fiber to the interior of the said tube.
Figure 5B:
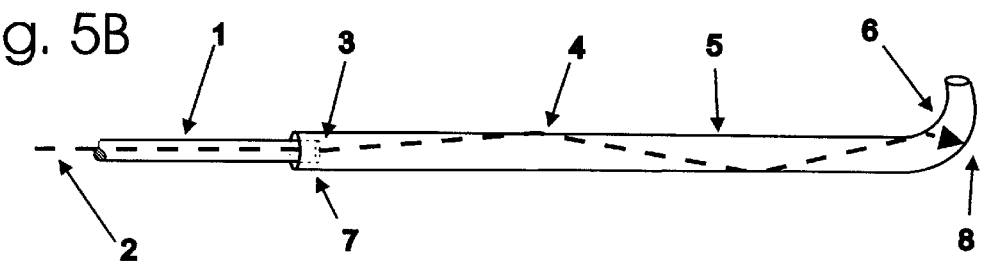
Figure 5C:
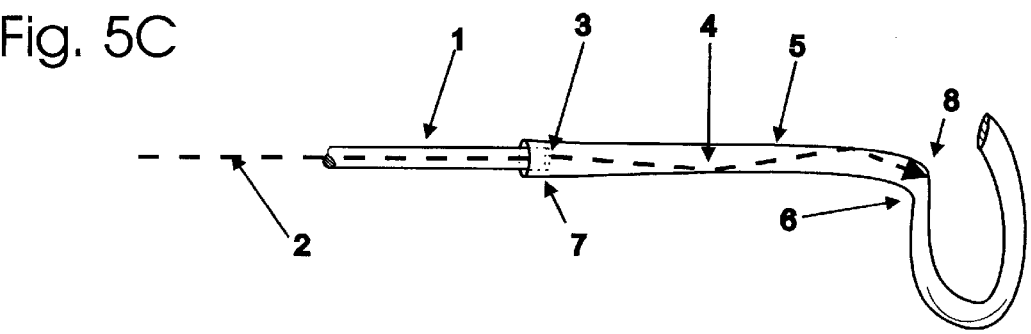
Figure 5D:
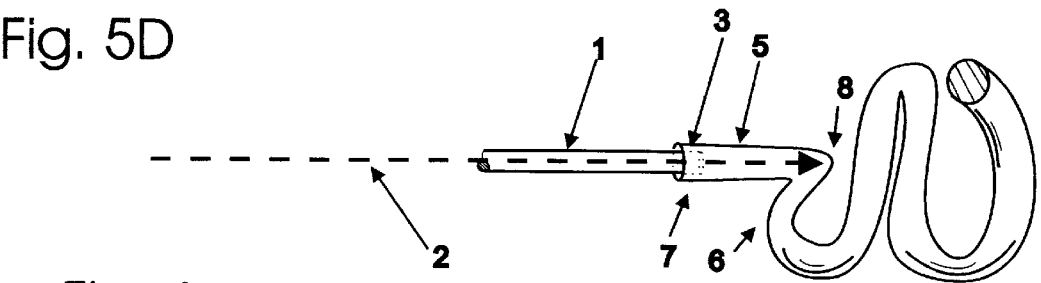
Figure 6:
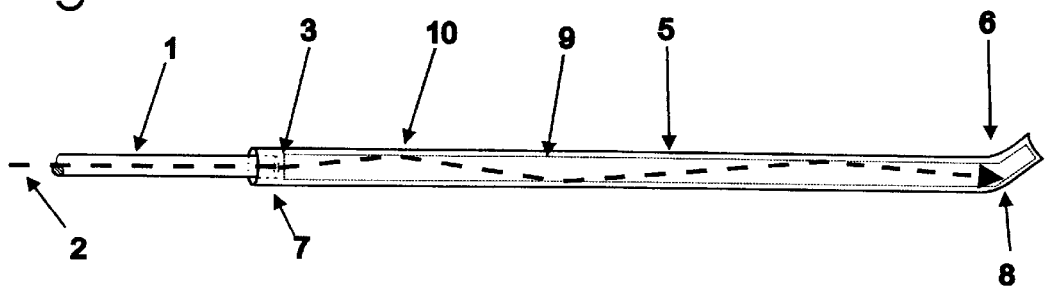
FIG. 6 is a perspective view of a SMA tube detachably attached to an optical fiber and with an optical fiber in the lumen of the tube.

Another preferred embodiment of the invention is shown in FIG. 6 and shows another length of optical fiber 9 detachably attached to the main optical fiber 1 by an optical fiber connection 7b. The inclusion of an optical fiber 9 into the lumen of the tube permits the more precise and predictable determination of the amount of bending of the tube that is required to transfer the photo-thermal energy on to the inner surface of the tube so bent. This preferred embodiment works in the same way as the first preferred embodiment immediately described above, not absorbing the photo-thermal energy 10 except that the optical fiber leaks at the point of sufficient bending 6, allowing the photo-thermal energy to be transmitted, normal to the longitudinal axis of the optical fiber, onto the surface of the tube 8, where it is absorbed. The interior surface of the SMA tube 5 can be treated and coated as described in the first preferred embodiment described above, but will in most cases be treated or coated to absorb as much photo-thermal energy as possible. The main optical fiber 1 can be attached to the SMA tube 5 by the same means 7 as described in the first preferred embodiment above. The two optical fibers can simply abut 7b permitting easy separation, using conventional optical fiber connecting methods.

Figure 7A:
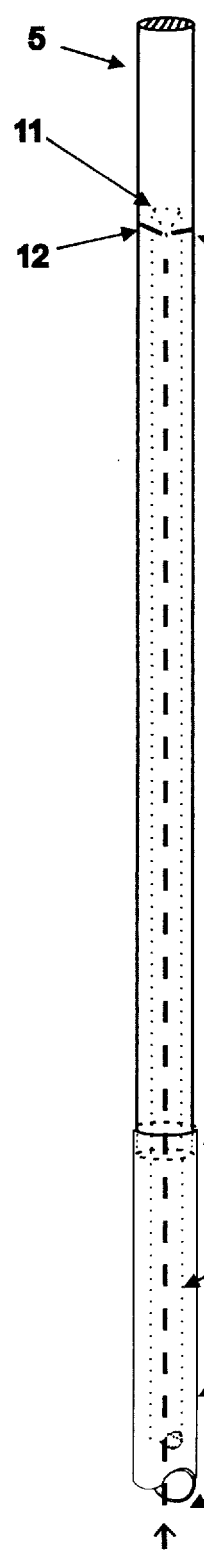
FIGS. 7A, 7B and 7C are perspective views of a SMA tube from which a side-firing optical fiber, that is delivering photo-thermal heating at its distal end, is being withdrawn from the SMA tube, simultaneously causing the SMA tube to recover its memorized high temperature shape; sequentially from FIG. 7A to FIG. 7C.
Figure 7B:
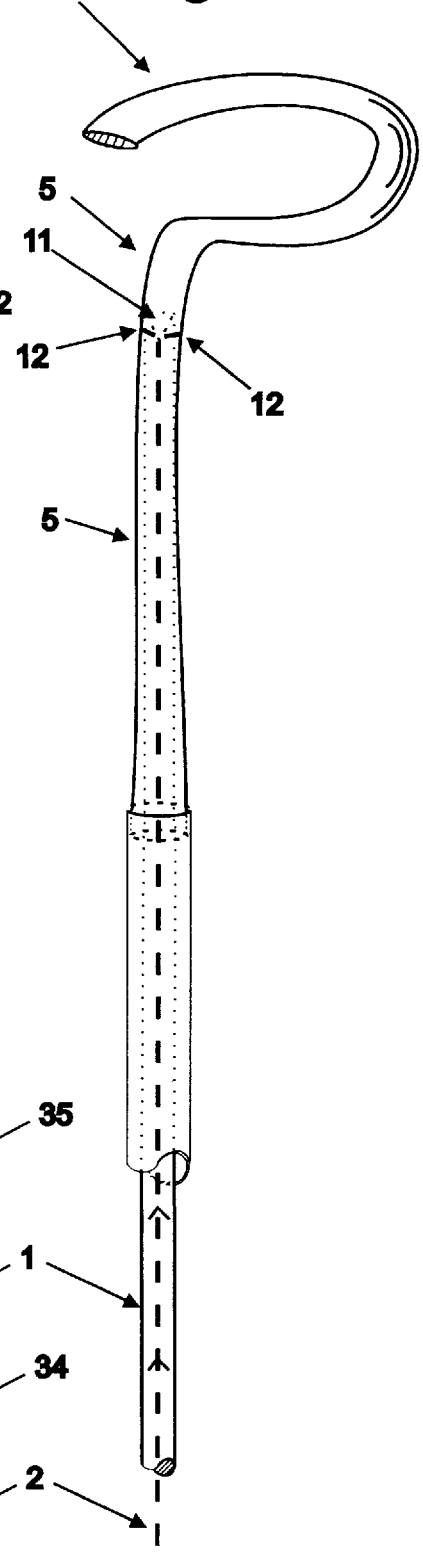
Figure 7C:
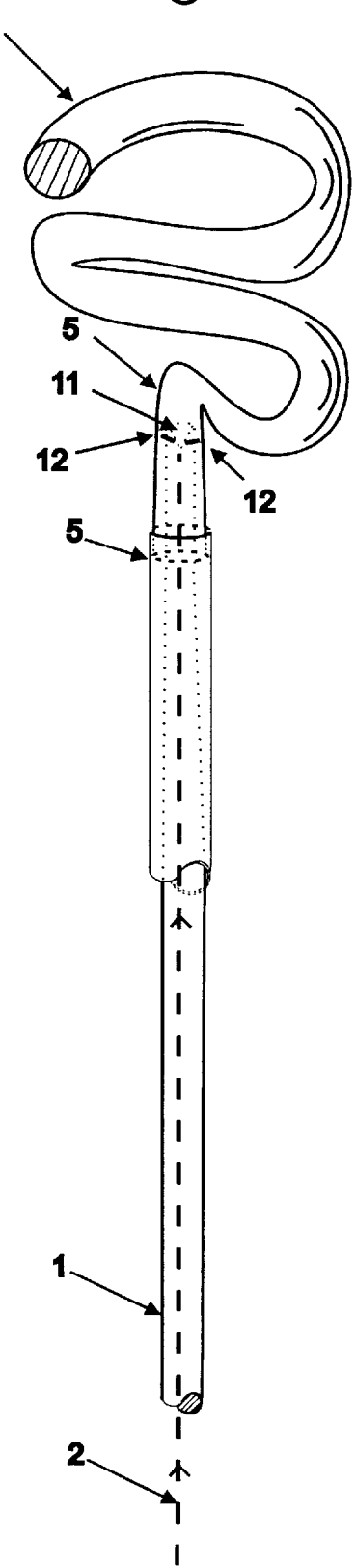

Another preferred embodiment of the invention is shown on FIGS. 7A, 7B, and 7C and comprises a SMA tube 5 with an optical fiber 1 in its lumen. The sequential illustrations show a SMA tube 5 that in this example begins as a relatively straight tube, as shown in FIG. 7A and then progressively returns to its high temperature memorized shape 6 as it is selectively heated by applying photo-thermal energy as illustrated in FIGS. 7B and 7C. The said SMA tube is detachably attached 35 to an extrusion catheter 34. The optical fiber 1 and the SMA tube 5 are not connected and the two can be moved independently of one another, along their longitudinal axes or radially around their longitudinal axes. The distal end of the optical fiber 1 is fitted or has fabricated into the optical fiber a means 11 by which the photo-thermal energy directed down the fiber is redirected in a direction approximately normal to the longitudinal axis of the optical fiber 12. Depending upon the type of optical fixture attached to the distal end of the said optical fiber 1 or type of modification of the distal end of the optical fiber 1, the beam can be redirected to the inner surface of the shape memory tube, and project onto that surface a variety of patterns of photo-thermal energy. There are many optical means that are well known to accomplish this redirection that involve reflection off a mirrored concave cone-shaped recess, mirrored bevels, as well as defracting and refracting means; all well know to the art.

Two examples of such optical means for redirecting the beam of photo-thermal energy 2 approximately normal to the longitudinal axis of the optical fiber are shown on FIG. 8 and FIG. 9. FIG. 8 illustrates a concave cone-shaped recess with a mirrored surface 14 on the distal end of the optical fiber. Such a lens will, depending upon the shape of the conical section, redirect the photo-thermal energy, traveling through the optical fiber in the direction of the said mirrored surface, approximately normal to the longitudinal axis of the optical fiber 12. FIG. 9 illustrates the pattern 16 that such an optical fiber would project on the inner surface of a SMA tube 5. That pattern would be the entire inner tube surface that is exposed to the photo-thermal energy projected by the said concave cone-shaped recess 14. Another example of such an optical means for redirecting the beam of photo-thermal energy is illustrated in FIG. 10, which has a beveled and mirrored surface 17 on the distal end of the optical fiber. Such a lens will, depending upon the details of its shape and the angle of the bevel, redirect the photo-thermal energy approximately normal 12 to the longitudinal axis of the optical fiber 1. The pattern of the projected photo-thermal energy on the interior of the tube will be different than the cone-shaped mirrored recess 14 described above. Instead it will project a patch 18 of thermal energy as illustrated in FIG. 11. The location of this patch can be changed by either rotating the optical fiber 1 around its longitudinal axis 20 or changing the relative location of the optical fiber 1 and the SMA tube 5 along their longitudinal axes 20. These are merely illustrations of two different patterns of photo-thermal energy that can be projected onto the interior surface of a SMA tube. By using such means to apply photo-thermal energy onto the inner surface of a SMA tube, the said tube an be heated above its $A_f$ temperature at any point or points along the length of the said tube using various optical means that would project various patterns. The deployment of such a device occurs in approximately the area that is heated, and further deployment can be halted by turning off the photo-thermal energy. The inner surface of the said SMA tube can also be treated and patterned, as described above to vary its absorbency to photo-thermal energy, but in most cases the inner surface of the tube using this preferred embodiment will be treated to have a high absorbency for the photo-thermal energy that is directed down the optical fiber 1.

As shown on FIG. 12, the inner surface of the SMA tube 5 can also have marks 19, etched, marked or printed by various conventional means to uniquely identify each part of the tube and that permit one to view 27 the location where the laser will project photo-thermal energy (only four of these example marks 19 are shown, for diagrammatic clarity). The marks are viewed by means of optical splitters 24, lens 26 and other conventional optical means that direct the return radiation 13 to a viewing lens 26. An auxiliary light source 25 can supply the illuminating light to illuminate the inside of the tube 15 and the marks 19 so they can be seen. This permits the exact positioning of the distal end 14 of the optical fiber in the tube prior to the delivery of photo-thermal energy onto that particular part of the tube.

In another preferred embodiment of the invention, instead of supplying photo-thermal energy to parts of the interior of the SMA tube, electrical energy is supplied by a probe 28 as shown in FIG. 13, FIG. 14 and FIG. 15. The probe is operated in the same way as the optical fiber in the previously described preferred embodiment. The only difference is that the heating of the parts of the interior of the SMA tube depends upon joule (resistance) heating of that part of the tube between the points where the two electrical contacts 30 or 31 contact the interior surface of the SMA tube 5. Insulated wires 29, are inside the probe and connect the external electrical power supply (not shown) to the contacts 30 or 31 on the distal end of the probe. The pattern of heating that occurs on the interior of the tube depends on the shape and location of the contacts on the probe. FIG. 13 shows an example of two ring contacts 30 that would cause a cylindrical section of the interior of the tube to be heated. FIG. 14 shows an example of two small contacts 31 that would cause a small spot of the interior of the tube to be heated. Of course the contacts can have many shapes and there may be more than two contacts as well. As in the preferred embodiment described immediately above, the probe can be rotated 32 about its longitudinal axis and the SMA tube 5 and probe 28 can be moved relative to one another along their longitudinal axes 32 to permit a multiplicity of points on the inner surface of the tube to be heated above the $A_f$ temperature.

Different optical fibers can be used for the same procedure. Some are more suitable for visually viewing the interior of the tube, while others are more suitable for heating. Several different fibers with different side-firing patterns could be used for the same procedure to shape the tube in various desired ways.

Another preferred embodiment of the invention is a means by which the location of the electrical contacts relative to particular locations of the tube can be viewed is illustrated on FIG. 15. A small optical fiber 1b similar in design to that illustrated in FIG. 10 would be contained within the electrical probe. Marks 19 would be made on the interior surface of the SMA tube 5 (not shown on FIG. 15) to uniquely identify each part of the said SMA tube. An aperture in the electrical probe 33 permits the marks on the interior of the tube to be viewed. This aperture could be a transparent window or a void. The marks 19 as well as the surface condition of the inner surface of the SMA tube 5 are viewed by means of a series of optical splitters 24 that directs the return radiation 13 to a viewing lens 26 and to the viewer 27. An auxiliary light source 25 can supply the illuminating light to illuminate the inner surface of the SMA tube 5 and the marks 19 so they can be seen and the condition of the inner surface of the said tube can be monitored, including its bending as it undergoes shape recovery. This permits the exact positioning of the probe 28 in the tube prior to the delivery of electrical energy onto that particular part of the tube and assists in determining the appropriate heat to be applied.

Another preferred embodiment of the present invention is illustrated on FIG. 16 and FIG. 17. The extrusion catheter 34 shown on FIGS. 7A, 7B and 7C can be attached to the SMA tube 5 by a number of mechanical means including for example: a friction coupling, a threaded coupling and a SMA coupling described below. The extrusion catheter is used to assist in positioning the SMA tube 5 for deployment and to position the said SMA tube as it is being deployed relative to the covering catheter 36, shown on FIG. 16. The covering catheter has a compliant and flexible distal end 37 that permits the SMA tube 5 to deploy without binding, but provides a thermal barrier between the part of the SMA tube that is being heated 8 and the surrounding area. The relative locations of the extrusion catheter and the covering catheter are controlled by simply pulling or pushing them in opposite directions or together along their longitudinal axes.

Figure 18D:
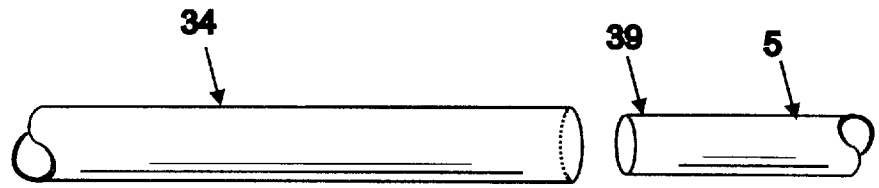

Another preferred embodiment of the invention is illustrated in FIGS. 18A, 18B, 18C and 18D. The means by which (35, FIG. 7A) the extrusion catheter 34 is detachably attached to the SMA tube 5, or the optical fiber 1 is detachably attached to the SMA tube (7, FIG. 5A), can be effected by many well known mechanical means including friction couplings, and threaded couplings. However the present invention permits the heating of small sections and patterned sections of the SMA tube 5. For example: a cylindrical section 38 of the detachably attached end of the SMA tube 5 could be expanded while below its $M_f$ temperature and could be friction fitted into the distal end of the extrusion catheter to form a secure connection 38b. Once placed and fully deployed, the said expanded cylindrical section of the said SMA tube 5 could be heated above its $A_f$ temperature using a side-firing optical fiber 1 or electrical probe 28 and the detachable end would shrink in circumference 39, as shown in FIG. 18C causing it to detach and separate from the extrusion catheter. The SMA tube could then be left in place and the extrusion catheter could be removed, as shown in FIG. 18D. Similarly a cylindrical section of the detachably attached proximal end of the SMA tube 5 could be shrunk below its $M_f$ temperature to allow for a coupling in which the said cylindrical section would encase the distal end of the extrusion catheter 34 or the distal end of the optical fiber 1.

The present invention can be used for many purposes, but is particularly suited to being placed into any body conduit or tubular organ. The system described herein has utility for supporting numerous body organs by using various sizes and of SMA tubes, optical fibers and in some cases extrusion catheters and cover catheters, that are varied to fit the organ in which they are being placed. These devices can be made from one or more tubes, to filter blood, provide structural support for body parts and passageways, and for cosmetic procedures.

While the present invention refers to an optical fiber, it is to be understood that a multiplicity or bundle of optical fibers could be used for the same purpose, and while the description refers to optical fibers 1 and an electrical probe 28 supplying energy to the inside of the tube 5 it is to be understood that these are merely examples of a larger class of energy guides that could also include microwave energy guides, or guides in which the energy is converted and redirected to the inside of the tube 5; for example an ultrasound generator near the distal end of the guide, powered by electric power and connected by wires running down the said guide. Similarly it is to be understood that the means by which the condition of the inside of the tube 5 is detected, monitored and reported by fiber optics, is just an example of a larger class of detection, monitoring and reporting means that would include for example a charged coupled device located at or near the distal end of the guide, connected by communication means to remote monitoring and reporting means.

While the present invention refers to shape memory alloy tubes, sometimes referred to as just tubes, it is to be understood that the invention includes tubes made of other materials that exhibit shape recovery when heated to an appropriate temperature. The references to shape memory alloy should then be considered to be by way of example only of a larger class of materials that exhibit similar properties.

It should also be understood that while the examples of tubes referred to in this disclosure and in the drawings are cylindrical, it is to be understood that tubes having a cylindrical cross-section are only examples of a larger class of tubes having many different cross-sections for example, triangular, square or star-shaped a combination thereof.

While the present invention has been described in conjunction with preferred embodiments, it is to be understood that modifications and variations may be resorted to without departing from the spirit and scope of the invention as those skilled in the art will readily understand. Such modifications and variations are considered to be within the purview and scope of the inventions and appended claims.

What is claimed is:

1. A system comprising: at least one tube having a proximal end, a distal end spaced from the proximal end, an inner surface and a lumen extending through the tube from the proximal end to the distal end, said lumen accommodating an energy guide, said energy guide delivering energy down the guide and thence being redirected by a redirecting means at approximately the distal end of the said guide, projecting energy onto the inner surface of said tube; said tube being made of SMA or other shape memory material that has a memorized shape, that is recovered or partly recovered with the application of thermal energy.

2. The system of claim 1 wherein at least a part of the inner surface of said tube is acid etched or coated to improve its reflectivity to photo-thermal radiation.

3. The system of claim 1 wherein the proximal end of said tube is detachably attached to a catheter.

4. The system of claim 1 wherein the distal end of the energy guide contains locating means selected from the group consisting of optical locating means, optical-electrical locating means, or electrical locating means for determining the position of the distal end of the energy guide relative to any location or point of reference on the inner surface of the tube in combination with marks on the interior of the tube, wherein said electrical locating means is a charged coupled device which is connected by communication means to remote monitoring and reporting means.

5. The system of claim 1, wherein that part of the said tube that is being heated by application of energy is thermally isolated from its surroundings by a catheter that has a flexible and compliant end.

6. The system of claim 1, in which the said tube is detachably attached to an elongated member having a distal end selected from the group consisting of an extrusion catheter or an optical fiber by changing the circumference of the proximal end of the said tube while below its $M_f$ temperature by mechanical deformation; the altered circumference being of such dimensions that the proximal end of the tube and the distal end of the elongated member can be snugly inserted into one another to form a stable coupling, said coupling, separating upon the application of photo-thermal energy or electrical energy sufficient to raise the temperature of that part of the said tube forming a coupling above the $A_f$ temperature.

7. The system of claim 1, wherein heating a portion of the tube by application of said photo thermal energy to the inner surface of the tube causes a transformation of said portion of said tube from a martensitic phase to an austenitic phase and wherein said transformation is detected by detecting the relative radiation emitted and reflected from the tube back down the optical fiber to a remote detection device, said thermal energy being selected from the group consisting of photo-thermal energy and joule heating.

8. The system of claim 1, wherein a temperature of a portion of said tube to which said photo thermal energy is applied is measured by detection of radiation emitted and reflected from the tube back down the optical fiber to a remote detection device.

9. The system of claim 1, wherein said tube undergoes bending as said memorized shape is at least partially recovered, and the bending of said tube is detected by visually monitoring the inner surface of the tube as it is recovering said memorized shape.

10. The system of claim 1, wherein selective application of said thermal energy to different parts of said tube produces, at different times, a plurality of different shapes in said tube.

11. The system of claim 1, wherein said tube comprises a supporting device of any desired shape, and is adapted to be positioned in a hollow body organ or hollow structure, and wherein said tube is deformable when completely martensitic into a compact form to allow for easy insertion in said body organ or hollow structure.

12. The system of claim 1, wherein said tube comprises a supporting device of any desired shape and is adapted to be positioned around a tubular body organ or tubular structure, and wherein said tube has an initial configuration that allows easy insertion in the body.

13. The system of claim 1, wherein said tube comprises a supporting device having a predetermined shape adapted to be positioned in a hollow body organ or hollow structure, said supporting device being deployed by the application of heat alone, by cooling and then heating, or by any combination thereof at temperatures that are suitable for the shape memory material chosen.

14. The system of claim 1, wherein application of said thermal energy to the inner surface of the tube, and an endothermic transformation from martensite to austenite that occurs during shape recovery, are effective to reduce the heat transfer to outside of said tube.

15. The system of claim 1, wherein a distal end of the energy guide is detachably attached to the proximal end of the tube.

16. The system of claim 1, wherein the energy guide is free to be guided in and out of said tube.

17. The system of claim 1, wherein energy is projected onto a part of the inner surface of the tube, with another part of the inner surface, onto which energy is not projected, acting as a heat sink.

18. The system of claim 1, wherein said system additionally comprises means for detecting, reporting and monitoring the condition of the tube and its inner surface.

19. The system of claim 1, wherein at least a part of the inner surface of the tube is coated or patterned to improve its reflectivity to photo-thermal radiation.

20. A system comprising: at least one tube having a proximal end, a distal end spaced from the proximal end, an inner surface and a lumen extending through the tube from the proximal end to the distal end, said tube being detachably attached to an optical fiber that delivers photo-thermal energy down the said fiber into the lumen of the said tube and to the inner surface of the said tube, said tube being made of shape memory alloy (SMA) or other shape memory material that has a memorized shape, that is recovered or partly recovered with the application of photo-thermal energy.

21. The system of claim 20 wherein said optical fiber is bent sufficiently to permit radiation to emit through the outer surface of the fiber to impinge upon the inner surface of said tube.

22. The system of claim 20, wherein energy is projected onto a part of the inner surface of the tube, with another part of the inner surface, onto which energy is not projected, acting as a heat sink.

23. A system comprising: at least one tube having a proximal end, a distal end spaced from the proximal end, and a lumen extending through the tube from the proximal end to the distal end, said lumen accommodating a side-firing optical fiber that is free to be guided in and out of the said tube, said optical fiber delivering photo-thermal energy, down the said optical fiber and thence being redirected by side-firing optic means at the distal end of the optical fiber, projecting the said photo-thermal energy onto part or parts of the inner surface of the said tube; said tube being made of SMA or other shape memory material that has a memorized shape, that is recovered or partly recovered with the application of photo-thermal energy.

24. The system of claim 23 wherein said side-firing optic means consists of an optical side-firing device attached to the distal end of the optical fiber.

25. The system of claim 23 wherein said side firing optic means is incorporated into the distal end of the optical fiber or is attached to it, said optic means adapted to project a predetermined pattern onto the inner surface of said tube.

26. A system comprising: at least one shape memory alloy (SMA) or shape memory material tube having a proximal end, a distal end spaced from the proximal end, and a lumen extending through the tube from the proximal end to the distal end, said lumen accommodating a probe that is free to be guided in and out of the said tube, said probe having at or near its distal end electrical contacts that contact with the inner surface of the tube; said electrical contacts being connected to wires that pass down through the probe to an electrical power source; said power source supplying an electrical potential between said two wires and said two contact points; said inner surface of the tube, providing a resistive conductor between the two contacts producing sufficient heat to heat the part of the tube between the two contacts for shape recovery to occur between the said two contacts, and those parts of the tube not so heated acting as a heat sink.

\* \* \* \* \*